United States Patent
Dyakonov et al.

(10) Patent No.: US 9,968,561 B2
(45) Date of Patent: May 15, 2018

(54) SILK-BASED CAPSULES (71) Applicant: PATHEON SOFTGELS INC, High Point, NC (US)

(72) Inventors: Tatyana Dyakonov, Greensboro, NC (US); Derek Bush, Belleair, FL (US); Saujanya L. Gosangari, Greensboro, NC (US); Yang Hue Chue, Greensboro, NC (US); Shingai Majuru, Mebane, NC (US); Aqeel Fatmi, High Point, NC (US)

(73) Assignee: Patheon Softgels Inc., High Point, NC (US)

( * ) Notice: Subject to any disclaimer, the term of this patent is extended or adjusted under 35 U.S.C. 154(b) by 0 days. days.

(21) Appl. No.: 14/776,325

(22) PCT Filed: Mar. 14, 2014

(86) PCT No.: PCT/US2014/026946
§ 371 (c)(1),
(2) Date: Sep. 14, 2015

(87) PCT Pub. No.: WO2014/152097
PCT Pub. Date: Sep. 25, 2014

(65) Prior Publication Data
US 2016/0045443 A1  Feb. 18, 2016

Related U.S. Application Data (60) Provisional application No. 61/790,890, filed on Mar. 15, 2013.

(51) Int. Cl.
*A61K 9/48* (2006.01)

(52) U.S. Cl.
CPC .......... *A61K 9/4825* (2013.01); *A61K 9/4833* (2013.01); *A61K 9/4866* (2013.01)

(58) Field of Classification Search
CPC .. A61K 9/4825; A61K 9/4833; A61K 9/4866; A61K 9/4816
See application file for complete search history.

(56) References Cited

U.S. PATENT DOCUMENTS

| | | | |
|---|---|---|---|
| 5,245,012 A | 9/1993 | Lombari et al. | |
| 5,252,285 A | 10/1993 | Lock | |
| 8,202,291 B1 | 6/2012 | Brister et al. | |
| 8,206,774 B2 | 6/2012 | Kaplan et al. | |
| 8,372,436 B2 * | 2/2013 | Scheibel | A61K 9/5052 424/490 |
| 8,906,444 B2 | 12/2014 | Kaplan et al. | |
| 8,993,065 B2 * | 3/2015 | Li | C08F 255/00 427/384 |
| 2008/0187707 A1 * | 8/2008 | Li | C08F 255/00 428/98 |
| 2009/0162439 A1 * | 6/2009 | Gobin | A01N 25/10 424/486 |
| 2010/0028451 A1 * | 2/2010 | Kaplan | A61K 9/1658 424/491 |
| 2012/0070427 A1 | 3/2012 | Tuna | |
| 2015/0056294 A1 * | 2/2015 | Kaplan | A61K 9/0019 424/499 |

FOREIGN PATENT DOCUMENTS

| | | | |
|---|---|---|---|
| EP | 3062785 A1 | 9/2016 | |
| JP | 2000212071 A1 | 8/2000 | |
| WO | WO 1997/08315 | 3/1997 | |
| WO | WO 2007014755 A1 * | 2/2007 | ........... A61K 9/5052 |
| WO | 2009100280 A2 | 8/2009 | |
| WO | WO 2011063990 A2 * | 6/2011 | ........... A61K 31/137 |
| WO | WO 2012145739 A1 * | 10/2012 | ........... A61K 9/0019 |

OTHER PUBLICATIONS

Dyakonov et al., Design and Characterization of a Silk-Fibroin-Based Drug Delivery Platform Using Naproxen as a Model Drug. Journal of Drug Delivery (2012), vol. 2012:10 pages.*
Huemmerich et al. Primary Structure Elements of Spider Dragline Silks and Their Contribution to Protein Solubility. Biochemistry 2004, 43, 13604-13612.*
Dyakonov et al., "Design and Characterization of a Silk-Fibroin-Based Drug Delivery Platform Using Naproxen as a Model Drug." J. Drug Deliv. 2012; 2012: Article ID 490514, 10 pages doi:10.1155/2012/490514. Published online Feb. 27, 2012.
Yang, et al., "Silk Fibroin Microspheres for Controlled Release" Poster Presentation (246) at 37th Annual Meeting & Exposition of the Controlled Release Society, Portland Oregon, Jul. 10-14, 2010.
European Search Report for EP Application No. 14767922.9, dated Sep. 16, 2016.

* cited by examiner

*Primary Examiner* — Robert A Wax
*Assistant Examiner* — Olga V Tcherkasskaya
(74) *Attorney, Agent, or Firm* — Brinks Gilson & Lione (57) ABSTRACT

A hard or soft capsule is disclosed comprising a shell and a fill material, wherein the shell comprises an interpenetrating network comprising a silk polymer and a film-forming natural polymer. A method of making a hard or soft capsule is also disclosed, comprising dissolving a silk protein in a solvent system to form a solubilized silk protein solution; mixing the solubilized silk protein solution with a film-forming natural polymer to form a homogenous shell material; and encapsulating a fill material with the homogenous shell material.

6 Claims, 3 Drawing Sheets

SILK-BASED CAPSULES

CROSS REFERENCE TO RELATED APPLICATIONS

This application is a national phase application under 35 U.S.C. § 371 from International Patent Application No. PCT/US2014/026946, filed on Mar. 14, 2014, which claims priority to U.S. Provisional Patent Application No. 61/790,890, filed Mar. 15, 2013, each of which is incorporated by reference herein in their entirety.

TECHNICAL FIELD

A hard or soft capsule is disclosed comprising a shell and a fill material, wherein the shell comprises a silk polymer and a film-forming polymer.

BACKGROUND

Hard and soft capsules are frequently preferred by patients as a dosage form. In hard and soft capsules, the drug-fill is contained within the capsule shell, resulting in a generally tasteless and odorless delivery system. In addition, many patients find it easier to swallow capsules than other oral dosage forms, such as tablets.

From the formulator's point of view, hard and soft capsules provide capabilities and options for dosage form design and formulation. For instance, hard capsules do not require the design of a compact capable of withstanding the handling required to produce a compressed tablet. In some cases, it is possible to direct-fill capsules with agents that otherwise require complex granulation procedures to be tableted. In addition, modern capsule-filling machines allow hard capsules to be filled with beads, granules, tablets, powders, and pumpable liquids. This capability provides the formulator with numerous options for designing delivery systems, or simply for separating incompatible substances within a single capsule.

Similarly, soft capsules are an attractive dosage form. In particular, soft capsules are useful for delivering many liquid formulations, including suspensions and pastes. Liquid ingredients are difficult to include in any other solid dosage form (e.g., as a tablet). Therefore, soft capsules are the exclusive means of formulating many liquid active pharmaceutical ingredients (APIs), including valproic acid, benzonatate, and oils, such as fish oil. Soft capsules are also particularly well suited for formulating many potent APIs (for example, where the dose is <100 μg). The highly reproducible filling process helps ensure each soft capsule contains the same dosage of API. In addition, soft capsules can be prepared under mild conditions. As a result, they are attractive for delivering, for example, temperature-sensitive active agents.

Despite their many advantages, existing hard and soft capsules are not compatible with all types of pharmaceutical formulations. For example, many active pharmaceutical ingredients (APIs) which have poor bioavailability (e.g., APIs classified as Class IV under the Biopharmaceutical Classification System (BCS)) require self-emulsifying drug delivery systems (SEDDS) or self-microemulsifying drug delivery systems (SMEDDS) which employ polyethoxylated surfactants. Many existing soft capsule shells are not compatible with high HLB-value surfactants. In particular, high-HLB-value surfactants can weaken the seams of soft capsules, resulting in fill leakage over time.

In addition, many controlled release formulations employ high melting point waxes that bind the API and provide the desired sustained release profile. The encapsulation of such formulations in existing soft capsules is problematic because the makeup of existing soft capsules requires that encapsulation be conducted in a narrow temperature range. Above this temperature range, the viscosity of the gel mass becomes too low to reliably form soft capsules with suitable stability (e.g., having properly sealed seams).

Further, enteric dosage forms are useful for protecting the contents of a dosage form from the gastric conditions of the stomach and/or to protect gastric tissue from an irritant material contained in the dosage form. Enteric-coated dosage forms are typically produced by a film coating process, where a thin film layer of an acid-insoluble (enteric) polymer is applied to the surface of a pre-manufactured dosage form. However, the enteric coating of conventional hard and capsules is problematic. Both hard and soft capsules can undergo thermally induced agglomeration and distortion of the capsule shell during coating. Moreover, the smoothness and elasticity of the capsule surface makes it difficult to form an intact adhering enteric coating, without a subcoating step to improve the surface of the capsule for coating. Finally, the enteric coatings cause the loss of the normally shiny and clear appearance of many capsule shells, which is a major reason for their popularity and acceptance.

SUMMARY

Silk-based hard and soft capsule delivery vehicles are provided. The hard and soft capsules comprise a capsule shell and a fill material. The capsule shell can be formed from a solubilized silk polymer and a film-forming polymer. The shell can further comprise a plasticizer, an enteric polymer, a gelling agent, a humectant, a preservative, a colorant, an opacifying agent, a flavoring agent, a sugar, a pH-modifying agent, or a combination thereof.

In some embodiments, the film-forming polymer comprises a natrual film-forming polymer. In some embodiments, the natrual film-forming polymer comprises gelatin. The film-forming polymer can be present in the capsule shell in an amount ranging from 20% to 70% by weight, based on the weight of the dried capsule shell.

The solubilized silk polymer can comprise silk fibroin (SF) obtained from natural silk fibers, such as *Bombyx mori* silk fibers. In some embodiments, the solubilized silk polymer comprises a silk fibroin powder. The solubilized silk polymer can have an average molecular weight ranging from 50 kDa to 450 kDa (e.g., from 50 kDa to 200 kDa). In certain embodiments, the solubilized silk polymer is substantially free of peptides having a molecular weight of 6,000 Da or less (e.g., the solubilized silk polymer can be substantially free of peptides having a molecular weight of 3,000 Da or less). The solubilized silk protein can be present in the capsule shell in an amount of 20% or less by weight, based on the weight of the dried capsule shell. For example, the solubilized silk protein can be present in the capsule shell in an amount of from greater than 0% to 10% by weight, based on the weight of the dried capsule shell.

As described above, the capsule shells are formed from a solubilized silk polymer and a film-forming polymer. The solubilized silk polymer can be a silk polymer, such as silk fibroin (SF), which has been processed such that it predominately adopts an amorphous (random coil) configuration in solution. When solidified in combination with a film-forming polymer to form a soft or hard capsule shell, the solubilized silk polymer can undergo a conformational transition from a random coil (soluble form) to a β-sheet form (insoluble form) produce an interpenetrating network (IPN) which comprises a silk polymer and a film-forming polymer. In some embodiments, the presence of the IPN can be confirmed by an absence of observable phase separation between the silk polymer and the film-forming polymer (e.g., when the shell is imaged using scanning electron microscopy (SEM)).

The silk-based hard and soft capsules can be more robust, exhibit better seams, and possess improved stability under storage, as compared to analogous capsules prepared without the solubilized silk polymer. In addition, the IPN can function to cross-link the capsule shell. This can retard the release of fill encapsulated within the capsule shell, a property that can be highly desirable for extended release formulations (e.g., for the delivery of active ingredients in the colon).

Also provided are methods of making silk-based hard and soft capsules. Silk-based hard and soft capsules can be prepared by dissolving a silk protein in a solvent system to form a solubilized silk protein solution, mixing the solubilized silk protein solution with a film-forming polymer to form a homogenous shell material; and encapsulating a fill material with the homogenous shell material. Optionally, one or more additives, such as plasticizers, may be added to the homogeneous shell material.

DETAILED DESCRIPTION

Silk-based hard and soft capsules and methods for their manufacture are disclosed. The hard and soft capsules include a capsule shell formed from a solubilized silk polymer and a film-forming polymer. The capsule shell defines an encapsulated space having a predetermined volume, which can contain a fill. The fill can be liquid, semisolid, or solid formulation comprising one or more active ingredients and, optionally, one or more pharmaceutically acceptable excipients.

The capsule shells are formed from a solubilized silk polymer and a film-forming .polymer. The solubilized silk polymer is added to the film-forming polymer to form a homogeneous mass. When solidified to form a soft or hard capsule shell, the solubilized silk polymer can undergo a conformational transition from a random coil (soluble form) to a β-sheet form (insoluble form) to induce crystallization and produce an interpenetrating network (IPN). The resulting soft or hard capsule shells can comprise an IPN, which comprises a silk polymer and a film-forming polymer.

The resulting capsule shells can be more robust, exhibit better seams, and possess improved stability under storage, as compared to analogous capsules prepared without the solubilized silk polymer. In addition, the IPN can function to cross-link the capsule shell. This can retard the release of fill encapsulated within the capsule shell, a property that can be highly desirable for delayed release formulations (e.g., for the delivery of active ingredients in the colon).

Solubilized Silk Polymer

The hard and soft capsule shells are formed from silk polymers. Silk polymers are natural biomaterials and exhibit many beneficial properties, including high strength and flexibility, biocompatibility, blood compatibility, water permeability, and oxygen permeability.

Raw silk fibers, referred to herein as "silk fibers," are silk fibers taken directly from a natural source, such as a cocoon formed by the larvae of a silkworm, such as the mulberry silkworm *Bombyx mori*.

Silk fibers are nearly pure protein fibers composed of a filament core protein, silk fibroin (SF), and a glue-like coating of a nonfilamentous protein, sericin. SF is characterized by repetitive hydrophobic and hydrophilic peptide sequences. Depending upon the source of the silk fibers (e.g., the cocoon strain), the SF content of the silk fibers can range from about 66.5% to 73.5% by weight, and the sericin content can range from about 26.5% to 33.5% by weight, based on the total weight of the silk fiber.

SF consists of heavy and light chain polypeptides of ~390 kDa and ~26 kDa, respectively, linked by a disulfide bond at the C-terminus of the two subunits. The primary structure of *Bombyx mori* SF is characterized by the presence of three amino acids in a roughly 3:2:1 ratio: glycine (45%), alanine (30%), and serine (12%); and the sequence is dominated by sequence [Gly-Ala-Gly-Ala-Gly-Ser]$_n$. SF chains also contain amino acids with bulky and polar side chains, in particular tyrosine, valine, as well as acidic amino acids.

The repetitive sequence of hydrophobic residues dominates the β-sheet structure, forming crystalline regions in SF fibers and films. The formation of these β-sheets results in insolubility in water. Hydrophobic regions of silk fibroin in aqueous solution assemble physically by hydrophobic interactions and eventually organize into hydrogels.

In some embodiments, the silk polymer comprises silk fibroin. In some embodiments, the silk fibroin is derived from silk fibers (e.g., silk fibers obtained from the cocoons of *Bombyx mori* larvae) that have been degummed to remove sericin along with other trace impurities, including wax matter, carbohydrates, inorganic material (e.g., mineral salts), and pigments. Silk fibers can be degummed using methods known in the art. See, for example, U.S. Pat. No. 5,252,285 to Lock. Sericin is insoluble in cold water; however, it is easily hydrolyzed to break down the sericin protein chains into lower molecular weight segments, which are easily dispersed or solubilized in hot water, leaving behind purified silk fibroin. For example, silk fibers can be degummed by heating the silk fibers in an aqueous acid, aqueous base (e.g., an aqueous solution of 0.02 M $Na_2CO_3$), or in solution comprising one or more enzymes (e.g., proteases) which cleave the sericin polymer chain.

In some embodiments, the silk polymer comprises a silk fibroin isolated from silk fibers that have been degummed to remove sericin. For example, in some embodiments, the silk polymer comprises less than 5% by weight sericin, based on the total weight of the solubilized silk polymer (e.g., less than 4.5% by weight sericin, less than 4.0% by weight sericin, less than 3.5% by weight sericin, less than 3.0% by weight sericin, less than 2.5% by weight sericin, less than 2.0% by weight sericin, less than 1.5% by weight sericin, or less than 1.0% by weight sericin).

In some embodiments, the silk polymer comprises a silk fiber that has been degummed to remove wax matter, carbohydrates, inorganic material, pigments, or combinations thereof. In some embodiments, the silk polymer can be essentially free of wax matter, carbohydrates, inorganic material, pigments, or combinations thereof (i.e., the solubilized silk polymer comprises less than 0.01% by weight wax matter, less than 0.01% by weight carbohydrates, less than 0.01% by weight inorganic material, less than 0.01% by weight pigments, or combinations thereof).

In some embodiments, the silk polymer comprises a silk fibroin powder. Suitable silk fibroin powders are commercially available, and include, for example silk fibroin powders available from Arch Chemicals, Inc (Atlanta, Ga., USA) sold under the trademark FIBRO-SILK®.

Other suitable silk polymers include spider silk obtained, for example, from Nephila clavipes, and genetically engineered silks, such as those obtained from bacteria, yeast, mammalian cells, transgenic animals, or transgenic plants. See, for example, WO 1997/08315 and U.S. Pat. No. 5,245,012 to Lombari et al.

In other embodiments, the silk polymer comprises a modified silk polymer. As used herein, the term "modified silk polymer" refers to a silk polymer that has been covalently modified, for example, by a diazonium coupling reaction to introduce a desired chemical moiety bonded to one or more tyrosine residue in the silk polymer. A "chemical moiety" is a chemical side group that can be used to change the physical properties of the silk polymer (e.g., hydrophobicity, hydrophilicity, or gelation behavior). In certain embodiments, the modified silk polymer can be covalently modified to increase its aqueous solubility, for example, by introducing a hydrophilic and/or charged moiety. Some non-limiting examples of chemical moieties include a sulfonic acid group, a carboxylic acid group, an amine group, a ketone group, an alkyl group, an alkoxy group, a thiol group, a disulfide group, a nitro group, an aromatic group, an ester group, an amide group, and/or a hydroxyl group. Modified silk polymers are known in the art. See for example, U.S. Pat. No. 8,206,774 to Kaplan, which is incorporated herein by reference for teaching of chemically modified silk polymers.

In some embodiments, the silk polymer (e.g., silk fibroin) has an average molecular weight ranging from 50 kDa to 450 kDa. In some embodiments, the silk polymer has a molecular weight of at least 50 kDa (e.g., at least 60 kDa, at least 70 kDa, at least 80 kDa, at least 90 kDa, at least 100 kDa, at least 110 kDa, at least 120 kDa, at least 130 kDa, at least 140 kDa, at least 150 kDa, at least 160 kDa, at least 170 kDa, at least 180 kDa, at least 190 kDa, at least 200 kDa, at least 210 kDa, at least 220 kDa, at least 230 kDa, at least 240 kDa, at least 250 kDa, at least 260 kDa, at least 270 kDa, at least 280 kDa, at least 290 kDa, at least 300 kDa, at least 310 kDa, at least 320 kDa, at least 330 kDa, at least 340 kDa, at least 350 kDa, at least 360 kDa, at least 370 kDa, at least 380 kDa, at least 390 kDa, at least 400 kDa, at least 410 kDa, at least 420 kDa, at least 430 kDa, or at least 440 kDa). In some embodiments, the silk polymer has a molecular weight of 450 kDa or less (e.g., 440 kDa or less, 430 kDa or less, 420 kDa or less, 410 kDa or less, 400 kDa or less, 390 kDa or less, 380 kDa or less, 370 kDa or less, 360 kDa or less, 350 kDa or less, 340 kDa or less, 330 kDa or less, 320 kDa or less, 310 kDa or less, 300 kDa or less, 290 kDa or less, 280 kDa or less, 270 kDa or less, 260 kDa or less, 250 kDa or less, 240 kDa or less, 230 kDa or less, 220 kDa or less, 210 kDa or less, 200 kDa or less, 190 kDa or less, 180 kDa or less, 170 kDa or less, 160 kDa or less, 150 kDa or less, 140 kDa or less, 130 kDa or less, 120 kDa or less, 110 kDa or less, 100 kDa or less, 90 kDa or less, 80 kDa or less, 70 kDa or less, or 60 kDa or less).

The molecular weight of the silk polymer can range from any of the minimum values to any of the maximum values described above. For example, the average molecular weight of the silk polymer can range from 50 kDa to 450 kDa (e.g., from 50 kDa to 200 kDa, from 50 kDa to 150 kDa, from 200 kDa to 400 kDa, or from 250 kDa to 400 kDa).

As described above, silk polymers, such as SF, contain repetitive sequence of hydrophobic residues. As a result, silk polymers have a tendency to form crystalline β-sheet structures. When in this primarily β-sheet conformation, silk polymers tend to be insoluble. As used herein, "insoluble" refers to silk polymers which can be pelleted by centrifugation, or which cannot be dissolved by immersion in, or rinsing with, water at 37° C. or less.

In certain embodiments, the silk polymer used to form the capsule shell is solubilized. Solubilized silk polymers are silk polymers that have been processed to increase their aqueous solubility prior to incorporation into the gel masses used to form the hard and soft capsule shells. The solubilized silk polymer can be processed such that the silk polymer predominately adopts an amorphous (random coil) configuration, allowing the silk polymer to be dissolved in an aqueous solution (i.e., the resulting solution is homogeneous, and the solubilized silk polymer cannot be pelleted by centrifugation).

In some embodiments, the solubilized silk polymer comprises SF in predominantly an amorphous (random coil) conformation. The conformation of the SF in solution can be analyzed by spectroscopy. For example, the structure of silk fibroin in solution can be evaluated by measuring characteristic spectroscopic signals (e.g., $^1$H NMR signals, IR absorption bands) associated with the amide moieties in the silk fibroin backbone. In some embodiments, the solubilized silk protein exhibits one or more spectroscopic signals (e.g., $^1$H NMR signals, IR absorption bands) characteristic of the presence of a random coil configuration. For example, in some embodiments, the silk polymer is solubilized by dissolving the silk polymer in a high ionic strength aqueous salt solution. The high ionic strength aqueous salt solution can be, for example, aqueous lithium thiocyanate (LiSCN), sodium thiocyanate (NaSCN), calcium thiocyanate (Ca(SCN)$_2$), magnesium thiocyanate (Mg(SCN)$_2$), calcium chloride (CaCl$_2$), lithium chloride (LiCl), lithium bromide (LiBr), zinc chloride (ZnCl$_2$), magnesium chloride (MgCl$_2$), copper salts such as copper nitrate (Cu(NO$_2$)$_2$), copper ethylene diamine (Cu(NH$_2$CH$_2$CH$_2$NH$_2$)$_2$ (OH)$_2$) and Cu(NH$_3$)$_4$(OH)$_2$, calcium nitrate (Ca(NO)$_2$), or Ajisawa's reagent (CaCl$_2$/ethanol/water).

The solubilized silk polymer can then be dialyzed using a dialysis membrane to remove salts and/or low molecular weight peptide impurities. For example, the solubilized silk polymer can be dialyzed against a cellulose membrane having a maximum molecular weight cut-off (MWCO) of less than 10 kDa. For example, the solubilized silk polymer can be dialyzed with a dialysis membrane having a MWCO ranging from 6 kDa to 8 kDa, or from 3 kDa to 5 kDa.

In some embodiments, the resulting solubilized silk polymer does not exhibit a Tyndall effect characteristic of colloidal dispersion. The Tyndall effect is observed when particles of a solid are dispersed in water but not dissolved. Colloids are insoluble solid particles that range in size from 1-1000 nm, and are suspended in a liquid phase. A Tyndall effect is created when a laser beam is scattered by its passage through a colloidal dispersion of non-dissolved particles. For such dispersions, the illumination of a visible path through the colloidal dispersion is observable. In contrast, in some embodiments, the resulting solubilized silk polymer does not exhibit a Tyndall effect characteristic of colloidal dispersion.

In some embodiments, the solubilized silk polymer is substantially free of peptides having a molecular weight of 10,000 Da or less (e.g., it is substantially free of peptides having a molecular weight of 9,000 Da or less, it is substantially free of peptides having a molecular weight of 8,000 Da or less, it is substantially free of peptides having a molecular weight of 7,000 Da or less, it is substantially free of peptides having a molecular weight of 6,000 Da or less, it is substantially free of peptides having a molecular weight of 5,000 Da or less, it is substantially free of peptides having a molecular weight of 4,000 Da or less, it is substantially free of peptides having a molecular weight of 3,000 Da or less, or it is substantially free of peptides having a molecular weight of 2,000 Da or less).

In some embodiments, the solubilized silk polymer is substantially free of sericin. For example, in some embodiments, the solubilized silk polymer comprises less than 0.1% by weight sericin (e.g., less than 0.075% by weight sericin, less than 0.05% by weight sericin, less than 0.025% by weight sericin, or less than 0.01% by weight sericin).

The solubilized silk protein can be present in the shell in an amount ranging from greater than 0% to 20% by weight, based on the weight of the dried capsule shell. For example, the solubilized silk protein can be present in the shell in an amount greater than 0% by weight, based on the weight of the dried capsule shell (e.g., greater than 0.1% by weight, greater than 0.25% by weight, greater than 0.50% by weight, greater than 0.75% by weight, greater than 1.0% by weight, greater than 1.5% by weight, greater than 2.0% by weight, greater than 2.5% by weight, greater than 3.0% by weight, greater than 3.5% by weight, greater than 4.0% by weight, greater than 4.5% by weight, greater than 5% by weight, greater than 6% by weight, greater than 7% by weight, greater than 8% by weight, greater than 9% by weight, greater than 10% by weight, greater than 11% by weight, greater than 12% by weight, greater than 13% by weight, greater than 14% by weight, greater than 15% by weight, greater than 16% by weight, greater than 17% by weight, greater than 18% by weight, or greater than 19% by weight). In some embodiments, the solubilized silk protein can be present in the shell in an amount less than 20% by weight, based on the total weight of the capsule shell (e.g., less than 19% by weight, less than 18% by weight, less than 17% by weight, less than 16% by weight, less than 15% by weight, less than 14% by weight, less than 13% by weight, less than 12% by weight, less than 11% by weight, less than 10% by weight, less than 9% by weight, less than 8% by weight, less than 7% by weight, less than 6% by weight, less than 5% by weight, less than 4.5% by weight, less than 4.0% by weight, less than 3.5% by weight, less than 3.0% by weight, less than 2.5% by weight, less than 2.0% by weight, less than 1.5% by weight, less than 1.0% by weight, less than 0.75% by weight, less than 0.50% by weight, or less than 0.25% by weight).

The solubilized silk protein can be present in the shell in an amount ranging from any of the minimum to any of the maximum values described above. For example, the solubilized silk protein can be present in the shell in an amount ranging from greater than 0% to 20% by weight, based on the weight of the dried capsule shell (e.g., from greater than 0% to 15% by weight, from greater than 0% to 10% by weight, from greater than 0% to 5.0% by weight, from greater than 0% to 3.0% by weight, or from greater than 0.25% to 5.0% by weight, or from greater than 0.25% to 3.0% by weight).

Film-Forming Polymer

The hard and soft capsule shells also include a film-forming polymer.

The film-forming polymer can be a natural film-forming polymer. In some embodiments, the film-forming natural polymer comprises gelatin. Gelatin is a mixture of peptides and proteins produced by partial hydrolysis of collagen extracted from the skin, boiled crushed bones, connective tissues, organs, and some intestines of animals, including, for example, domesticated cattle, chicken, and pigs. In many respects, the chemical composition of gelatin is similar to that of collagen. The natural molecular bonds between individual partially hydrolyzed collagen strands in gelatin are broken down into a form that can rearrange. Gelatin can melt to a liquid when heated, and can re-solidify upon cooling. Gelatin can form a high viscosity solution in hot water, which sets upon cooling to form a semi-solid colloid gel.

Gelatin solutions can show viscoelastic flow and streaming birefringence. As described above, gelatin can swell and form a semi-solid material in the presence of cold water. However, gelatin is readily soluble in hot water. The solubility of the gelatin is determined by the method of manufacture. Gelatin can be dispersed in a relatively concentrated acid. Such dispersions can be stable for several days (e.g., up to 15 days) with little or no chemical changes and are suitable for coating purposes or for extrusion into a precipitating bath.

Suitable gelatins include gelatins derived from pork skins, pork and cattle bones, or split cattle hides. Gelatin can be classified as either Type A or Type B gelatin. Type A gelatin is derived from the acid hydrolysis of collagen, while Type B gelatin is derived from the alkaline hydrolysis of collagen. Traditionally, bovine bones and skins have been used as raw materials for manufacturing Type A and Type B gelatin while porcine skins have been used extensively for manufacturing Type A gelatin. In general, acid processed gelatins form stronger gels than lime-processed gelatins of the same average molecular weight. Gelatin is available in various grades and, in turn, has different average molecular weights. Commercially, gelatins tend to be graded in terms of their gel strengths (Bloom value) under standard test conditions, although viscosity is generally also an important parameter for encapsulation applications. The Bloom strength test determines the force (e.g., in grams) needed by a probe to deflect the surface of the gel without breaking it. The cylindrical probe used for the test has a diameter of about 0.5 inch and the deformation of the gel tested can be about 4 mm. The result is expressed in Bloom (grams).

In some embodiments, the gelatin has a Bloom strength (expressed in Bloom (grams)) of between 30 and 300 Bloom. In some embodiments, the gelatin has a Bloom strength of at least 30 Bloom (e.g., at least 50 Bloom, at least 100 Bloom, at least 150 Bloom, at least 200 Bloom, or at least 250 Bloom). In some cases, the gelatin has a Bloom strength of 300 Bloom or less (e.g., 250 Bloom or less, 200 Bloom or less, 150 Bloom or less, 100 Bloom or less, or 50 Bloom or less).

The gelatin can have a Bloom strength ranging from any of the minimum to any of the maximum values described above. For example, the gelatin can have a Bloom strength ranging from 30 to 300 Bloom (e.g., from 50 to 250 Bloom, from 100 to 250 Bloom, or from 150 to 200 Bloom).

Molecular weight values are not normally used for gelatins, since there is no universally accepted test procedure for gelatin and the values for average molecular weights can vary dependent on the test method and procedure used. However, based on a size exclusion HPLC method, suitable gelatins can have weight average molecular weights in the range 80,000-200,000 Daltons. Lower molecular weight gelatins (30 kDa-80 kDa) are also available, and non-gelling gelatins can be produced by deliberately hydrolyzing the gelatins to a weight average molecular weight of the order 5,000-30,000 Daltons.

Other suitable natural film-forming polymers include polysaccharides, such as carrageenans (e.g., kappa carrageenan, iota carrageenan, lambda carrageenan and combinations thereof), glucomannans, starches (e.g., unmodified starch and modified pregelatinized starch), and combinations thereof For example, in some embodiments, the film-forming natural polymers can comprise a carrageenan. Carrageenans are natural polysaccharide hydrocolloids that are derived from seaweed. Carrageenans can include a linear carbohydrate polymer of repeating sugar units, without a significant degree of substitution or branching. Carrageenans can be categorized based on their degree of sulfation. Most, if not all, of the galactose units in the carrageenan molecule possess a sulfate ester group. Kappa-carrageenan has one sulfate per disaccharide. Iota-carrageenan has two sulfates per disaccharide. Lambda carrageenan has three sulfates per disaccharide. Minor forms of carrageenan (e.g., mu carrageenan and nu carrageenan) can also be used.

The film-forming polymer can be a synthetic or semi-synthetic film-forming polymer. Suitable synthetic and semi-synthetic film-forming polymers include, for example, hydroxypropyl methyl cellulose, methyl cellulose, hydroxypropyl methyl cellulose acetate succinate, hydroxypropyl methyl cellulose phthalate, cellulose acetate phthalate, and acrylates such as poly(meth)acrylate.

The film-forming polymer can be present in the capsule shell in an amount ranging from 20% to 70% by weight, based on the total weight of the dried capsule shell. In some embodiments, the film-forming polymer can be present in the capsule shell in an amount greater than 20% by weight, based on the total weight of the dried capsule shell (e.g., greater than 25% by weight, greater than 30% by weight, greater than 35% by weight, greater than 40% by weight, greater than 45% by weight, greater than 50% by weight, greater than 55% by weight, greater than 60% by weight, or greater than 65% by weight). In some embodiments, the film-forming polymer can be present in the capsule shell in an amount less than 70% by weight, based on the total weight of the dried capsule shell (e.g., less than 65% by weight, less than 60% by weight, less than 55% by weight, less than 50% by weight, less than 45% by weight, less than 40% by weight, less than 35% by weight, less than 30% by weight, or less than 25% by weight).

The amount of film-forming polymer present in the capsule shell can range from any of the minimum to any of the maximum values described above. For example amount of film-forming polymer present in the capsule shell can range from 20% to 70% by weight, based on the weight of the dried capsule shell (e.g., from 30% to 70% by weight, or from 35% to 65% by weight).

Additional Components of the Shell

The shell can further comprise one or more additional components. For example, the capsule shell further comprises a plasticized, an enteric polymer, a gelling agent, a humectant, a preservative, a colorant, an opacifying agent, a flavoring agent, a sugar, a pH-modifying agent, or a combination thereof.

In some embodiments, the shell further comprises a plasticizer. Examples of suitable plasticizers include polyalcohols with 3 to 6 carbon atoms (e.g., glycerol), sorbitol, sorbitan, maltitol, polyethylene glycol, citric acid, citric acid esters, triethyl citrate, and combinations thereof. In certain embodiments, shell comprises a plasticizer effective to influence the conformation of the solubilized silk polymer (e.g., effective to influence β-sheet formation). For example, the shell can include a polyalcohol having from 3 to 6 carbon atoms, such as glycerol.

In certain embodiments, the hard or soft capsule shell includes glycerol. Glycerol (i.e., glycerine or glycerin) is a colorless, odorless, viscous liquid that is widely used in pharmaceutical formulations. Glycerol is a polyol containing three hydroxyl groups that are responsible for its solubility in water and its hygroscopic nature. Glycerol is sweet tasting and has low toxicity. For human consumption, glycerol is classified by the U.S. FDA among the sugar alcohols as a caloric macronutrient.

In some embodiments, the plasticizer is sorbitol. Sorbitol is a sugar alcohol that the human body metabolizes slowly. It can be obtained by reducing the aldehyde group of glucose to a hydroxyl group. Sorbitol is naturally found in apples, pears, peaches, and prunes. A special grade of aqueous sorbitol solution can be used in soft capsule shells as a plasticizer to prevent the soft capsules from becoming brittle. In some embodiments, sorbitol is included in capsule shells that will contain polyethylene glycol as component of the fill material.

In some embodiments, one or more plasticizers are present in the capsule shell in an amount ranging from 8% to 40% by weight, based on the weight of the dried capsule shell. In some embodiments, one or more plasticizers are present in the capsule shell in an amount greater than 8% by weight, based on the weight of the dried capsule shell (e.g., greater than 10% by weight, greater than 15% by weight, greater than 20% by weight, greater than 25% by weight, greater than 30% by weight, or greater than 35% by weight). In some embodiments, one or more plasticizers are present in the capsule shell in an amount less than 40% by weight, based on the weight of the dried capsule shell (e.g., less than 35% by weight, less than 30% by weight, less than 25% by weight, less than 20% by weight, less than 15% by weight, or less than 10% by weight). In certain embodiments, one or more plasticizers are present in the capsule shell in an amount of from 10% to 40% by weight, based on the weight of the dried capsule shell. The capsule shell can further include one or more gastric resistant polymers to provide enteric properties to the capsule shell. The gastric resistant polymers can be gastric resistant natural polymers, gastric resistant synthetic polymers, or combinations thereof. The gastric resistant polymer can be included within the gel mass at the time of shell manufacture. The capsule shell can include one or more layer formed from a composition that includes the gastric resistant polymer, or can include multiple layers including at least an outside coating layer that includes the gastric resistant polymer.

In some embodiments, the capsule shell can further be formed of a gastric resistant natural polymer, including a polysaccharide such as pectin and/or alginates. Other suitable gastric-resistant polymers include acrylic and methacrylate acid copolymers, cellulose acetate phthalate (CAP), cellulose acetate butyrate, hydroxypropylmethylcellulose phthalate (HPMCP), algenic acid salts such as sodium or potassium alginate, or shellac. Poly(methacylic acid-co-methyl methacrylate) anionic copolymers based on methacrylic acid and methyl methacrylate are particularly stable and are preferred in some embodiments. Poly(meth)acrylates (methacrylic acid copolymer), available under the trade name EUDRAGIT ® (Evonik Industries AG, Essen, Germany), are provided as powder or aqueous dispersions. In some aspects, the methacrylic acid copolymer can be EUDRAGIT® L 30 D-55; EUDRAGIT® L 100-55; EUDRAGIT® L 100; EUDRAGIT® L 12.5; EUDRAGIT® S 100; EUDRAGIT® S 12.5; EUDRAGIT® FS 30 D; EUDRAGIT® E 100; EUDRAGIT® E 12.5; EUDRAGIT® E PO; EUDRAGIT® RL 100; EUDRAGIT® RL PO; EUDRAGIT® RL 30 D; EUDRAGIT® RL 12.5; EUDRAGIT® RS 100; EUDRAGIT® RS PO; EUDRAGIT® RS 30 D; EUDRAGIT® RS 12.5; EUDRAGIT® NE 30 D; EUDRAGIT® NE 40 D; EUDRAGIT® NM 30 D; or other poly(meth)acrylate polymers. In one aspect, the gastric resistant polymer is EUDRAGIT® L 100, a methacrylic acid copolymer, Type A. Acid-insoluble polymer specifications are detailed in the United States Pharmacopoeia and in various monographs. The gastric resistant polymer can be included in the capsule shell in an amount ranging from greater than 0% by weight to 10% by weight, based on the weight of the dried capsule shell.

The capsule shell of the soft elastic capsule can further be formed of one or more gelling agents. The gelling agent can include, for example, one or more divalent cations. The divalent cations can be provided as divalent cation salts (e.g., calcium salts and magnesium salts). When included, the concentration of the gelling agent can be greater than 0% by weight and less than about 2% by weight of the dried capsule shell (e.g., less than about 1.5%, less than about 1.0%, or less than about 0.5% by weight of the dried capsule shell).

Optionally, the capsule shells can include one or more viscosity modifiers. Examples of suitable viscosity modifiers include guar gum, locust bean gum, xanthan gum, agar, and gellan gum. The viscosity modifier can be included in the capsule shell in an amount of greater than 0% by weight and less than 10% by weight of the dried capsule shell (e.g., less than 9%, less than 8%, less than 7%, less than 6%, less than 5%, less than 4%, less than 3%, less than 2%, less than 1%, or less than 0.5% by weight of the dried capsule shell).

The capsule shell can be prepared as a transparent or translucent capsule shell. In some embodiments, the capsule shell can be semi-transparent, semi-opaque, or opaque. Optionally, the opaque capsule shells are prepared using titanium dioxide, which can protect light sensitive active ingredients from degradation. The capsule shells can further include a colorant to color the capsules. Examples of suitable colorants include FD&C and D&C dyes, iron oxides, and natural colorants. Optionally, the capsule can be imprinted or have a decorative coating. The capsule shell can be prepared to have only one compartment (i.e., the capsule shell does not contain multiple compartments).

Fill Materials

The hard and soft capsules can further include a fill encapsulated within the capsule shell. The fill can be a liquid (e.g., a solution, suspension, or dispersion), a semisolid (e.g., a paste or gel), or a solid formulation. The fill can comprise one or more active ingredients and, optionally, one or more pharmaceutically acceptable excipients.

Suitable active ingredients can include, for example, pharmaceutical agents (e.g., therapeutic agents, prophylactic agents, and diagnostic agents), nutraceuticals, vitamins, minerals, and combinations thereof.

Examples of pharmaceutical agents that can be included as an active ingredient include agents classified as, for example, an adrenocortical steroid, adrenocortical suppressant, aldosterone antagonist, amino acid, anabolic steroid, androgen, antagonist, anthelmintic, anti-acne agent, anti-adrenergic, anti-allergic, anti-amebic, anti-androgen, anti-anemic, anti-anginal, anti-arthritic, anti-asthmatic, anti-atherosclerotic, antibacterial, anticholelithic, anticholelithogenic, anticholinergic, anticoagulant, anticoccidal, antidiabetic, antidiarrheal, antidiuretic, antidote, anti-estrogen, antifibrinolytic, antifungal, antiglaucoma agent, antihemophilic, antihemorrhagic, antihistamine, antihyperlipidemia, antihyperlipoproteinemic, antihypertensive, antihypotensive, anti-infective, anti-infective, anti-inflammatory, antikeratinizing agent, antimalarial, antimicrobial, antimitotic, antimycotic, antineoplastic, antineutropenic, antiparasitic, antiperistaltic, antpneumocystic, antiproliferative, antiprostatic hypertrophy, antiprotozoal, antipruritic, antipsoriatic, antirheumatic, antischistosomal, antiseborrheic, antisecretory, antispasmodic, antithrombotic, antitussive, anti-ulcerative, anti-urolithic, antiviral, appetite suppressant, benign prostatic hyperplasia therapy agent, bone resorption inhibitor, bronchodilator, carbonic anhydrase inhibitor, cardiac depressant, cardioprotectant, cardiotonic, cardiovascular agent, choleretic, cholinergic, cholinergic agonist, cholinesterase deactivator, coccidiostat, contrasting agent, diagnostic aid, diuretic, ectoparasiticide, enzyme inhibitor, estrogen, fibrinolytic, free oxygen radical scavenger, glucocorticoid, gonad-stimulating principle, hair growth stimulant, hemostatic, hormone, hypocholesterolemic, hypoglycemic, hypolipidemic, hypotensive, imaging agent, immunizing agent, immunomodulator, immunoregulator, immunostimulant, immunosuppressant, impotence therapy adjunct, inhibitor, keratolytic, LHRH agonist, liver disorder treatment, luteolysin, mucolytic, mydriatic, nasal decongestant, neuromuscular blocking agent, non-hormonal sterol derivative, oxytocic, plasminogen activator, platelet activating factor antagonist, platelet aggregation inhibitor, potentiator, progestin, prostaglandin, prostate growth inhibitor, prothyrotropin, radioactive agent, regulator, relaxant, repartitioning agent, scabicide, sclerosing agent, selective adenosine A1 antagonist, steroid, suppressant, symptomatic multiple sclerosis, synergist, thyroid hormone, thyroid inhibitor, thyromimetic, amyotrophic lateral sclerosis agents, Paget's disease agents, unstable angina agents, uricosuric, vasoconstrictor, vasodilator, vulnerary, wound healing agent, and xanthine oxidase inhibitor.

Further examples of suitable pharmaceutical agents include those as listed in the Merck Index (13th Edition, Wiley, 2001), The United States Pharmacopeia-National Formulary (USP-NF), and the FDA's Orange book.

Examples of nutraceuticals include, but are not limited to, amino acids, terpenoids (e.g., carotenoid terpenoids and non-carotenoid terpenoids), herbal supplements, homeopathic supplements, glandular supplements, polyphenolics, flavonoid polyphenolics, phenolic acids, curcumin, resveratrol, lignans, glucosinolates, isothiocyanates, indoles, thiosulfonates, phytosterols, anthraquinones, capsaicin, piperine, chlorophyll, betaine, oxalic acid, acetyl-L-carnitine, allantoin, androsterondiol, androsterondione, betaine (trimethylglycine), caffeine, calcium pyvurate (pyruvic acid), carnitine, carnosine, carotene, carotenoid, choline, chlorogenic acid, cholic acid, chondroitin sulfate, chondroitin sulfate, cholestin, chrysin, coenzyme Q10, conjugated linoleic acid, corosolic acid, creatine, dehydroepiandrosterone, dichlorophen, diindolymethane, dimethylglycine, dimercapto succinic Acid, ebselen, ellagic acid, enzymes, fisetin, formonetin, glucaric acid (glucarate), glucosamine (HCl or sulfate), glucosamine (N-acetyl), glutathione, hesperidine, hydroxy-3-methylbutyric Acid, 5-hydroxytryptophan, indole-3-carbinol, inositol, isothiocyanates, linolenic acid-gamma, lipoic acid (alpha), melatonin, methylsulfonylmethane, minerals, naringin, pancreatin, para-aminobenzoic acid, paraben (methyl or propyl), phenolics, phosphatidylcholine, phosphatidylserine, phospholipids, phytosterols, progesterone, pregnenolone, quercetin, resveratrol, D-ribose, rutin, S-adenosylmethionine, salicylic acid, sulforaphane, tartaric acid, taxifolin, tetrahydropalmatine, theophyline, theobromine, tigogenin, troxerutin, tryptophan, tocotrienol (alpha, beta & gamma), zeaxanthin, gingko biloba, ginger, cat's claw, hypericum, aloe vera, evening primrose, garlic, capsicum, dong quai, ginseng, feverview, fenugreek, echinacea, green tea, marshmallow, saw palmetto, tea tree oil, fish oil, payllium, kava-kava, licorice root, manonia aquifolium, hawthorne, hohimbr, tumeric, witch Hazel, valerian, mistletoe, bilberry, bee pollen, peppermint oil, beta-carotene, genistein, lutein, lycopene, the polyphenols, and the like.

Further examples of suitable nutraceuticals include those listed in Handbook of Nutraceuticals and Functional Foods, edited by Robert E. C. Wildman, CRC Press (2001).

Other useful pharmaceutical agents that can be included as an active ingredients include fish oils, egg oils, squid oils, krill oils, nut oils, seed oils; soy oils, avocado oils, seabuckthorn seed or berry oils, clary sage seed oils, algal oils, flaxseed oils, sacha ichi oils, echium oils, hemp oils, omega-3 fatty acids, polyunsaturated omega-3 fatty acids, hexadecatrienoic acid (HTA), alpha-linolenic acid (ALA), stearidonic acid (SDA), eicosatrienoic acid (ETE), eicosatetraenoic acid (ETA), eicosapentaenoic acid (EPA, timnodonic acid), heneicosapentaenoic acid (HPA), docosapentaenoic acid (DPA), clupanodonic acid), docosahexaenoic acid (DHA, cervonic acid), tetracosapentaenoic acid, tetracosahexaenoic acid (nisinic acid), and free acids, etheyl esters, or other esters or salts thereof. In some aspects, the pharmaceutical agent is a highly purified omega-3 fatty acid, ester, or salt thereof.

Vitamins can include organic substances that are typically considered essential for the normal growth and activity of a subject (e.g., a human or non-human animal patient to whom the composition is to be administered). Examples of vitamins include, but are not limited to vitamin A (retinol), B1 (thiamine), B2 (riboflavin), B complex, B6 (pyridoxine), B12 (cobalamin), C (ascorbic acid), D (cholecalciferol), E (tocopherol), F (linoleic acid), G, H (biotin), and K, and choline, folic acid, inositol, niacin, pantothenic acid, and para-aminobenzoic acid.

Vitamins can include naturally occurring inorganic substances that are typically considered essential for the normal growth and activity of a subject (e.g., a human or non-human animal patient to whom the composition is to be administered). Examples of minerals include, but are not limited to, boron, calcium, chromium, copper, iron, magnesium, manganese, molybdenum, nickel, phosphorus, selenium, silicon, tin, vanadium, and zinc.

The fill can optionally include one or more pharmaceutically acceptable excipients. Examples of pharmaceutically acceptable excipients include buffers, such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers, such as polyvinyl pyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN® (ICI, Inc.; Bridgewater, N.J.), polyethylene glycol (PEG), and PLURONICS™ (BASF; Florham Park, N.J.). Diluents commonly used in the art can also be encapsulated within the shell, including water or other solvents, solubilizing agents, and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, sesame oil, glycerol, tetrahydrofurfuryl alcohol, polyethylene glycols, and fatty acid esters of sorbitan, and mixtures of these substances.

In certain embodiments, the fill is a liquid (e.g., a solution, suspension, or dispersion) or a semisolid (e.g., a paste or gel). In some cases, the active ingredient can be innately a liquid or semisolid. In certain cases, the active ingredient can be prepared as a liquid or semisolid by, for example, by dissolving or otherwise mixing an active ingredient and optionally one or more pharmaceutical adjuvants in a carrier, such as, for example, water, saline, aqueous dextrose, glycerol, glycols (e.g., propylene glycol or polyethylene glycol), ethanol, fatty acids, glycerides, oils, sterols, phospholipids, and the like, to thereby form a solution.

In some embodiments, the active ingredient can be dispersed or suspended in the liquid carrier. In some embodiments, the active ingredient can be prepared in a self-emulsifying/microemulsifying drug delivery system (SEDDS/SMEDDS). Optionally, the SEDDS system can include an oil, a surfactant, a cosurfactant or solubilizer, and the active ingredient.

The liquid active ingredients can be prepared to contain the active ingredient in the range of 0.005% to 100%, with the balance made up from non-toxic carrier. Methods for preparation of these compositions are known to those skilled in the art. See, for example, Remington's Pharmaceutical Sciences, Mack Publishing Company, Easton, Pa., $15^{th}$ Edition, 1975. The liquid fill can contain 0.001% to 100%, 0.1% to 95%, 1% to 90%, 5% to 70%, or 10% to 50% by weight active ingredient.

Methods of Manufacture

Also provided are methods of making silk-based hard and soft capsules.

Silk-based hard and soft capsules can be prepared by dissolving a silk protein in a solvent system to form a solubilized silk protein solution, mixing the solubilized silk protein solution with a film-forming polymer to form a homogenous shell material; and encapsulating a fill material with the homogenous shell material. Optionally, one or more additives, such as plasticizers, may be added to the homogeneous shell material.

In some embodiments, the concentration of the solubilized silk protein (e.g., silk fibroin) in the solubilized silk protein solution is 10% by weight or less, based on the total weight of the solubilized silk protein solution. For example, the concentration of the solubilized silk protein (e.g., silk fibroin) in the solubilized silk protein solution can range from 4% to 8%, by weight. In some embodiments, the homogenous shell material can comprise (w/w) greater than 0% by weight to 10% solubilized silk polymer, 40-50% film-forming polymer, 20-30% plasticizer, and 30-40% purified water. The primary difference between soft and hard capsules is the amount of plasticizer present in the capsule shell. Most of the water is subsequently lost during capsule drying. In some embodiments, the dried capsule shell can comprise less than 10% by weight water, based on the weight of the dried capsule shell. For example, the dried capsule shell can comprise from 6% to 10% by weight water, based on the weight of the dried capsule shell (e.g., from 6% to 8% by weight water, or from 8% to 10% by weight water).

The ingredients, including the solubilized silk protein solution and film-forming polymer, are combined to form a homogenous shell material (sometimes referred to in the art as a molten gel mass) using either a cold melt or a hot melt process. The prepared a homogenous shell material can then be transferred to preheated, temperature-controlled, jacketed holding tanks where the homogenous shell material can be (e.g., at a temperature ranging from 50-60° C.) until used for encapsulation. In some embodiments, the homogeneous shell material can have a viscosity of from 5,000 cP to 30,000 cP at 60° C.

The cold melt process can involve mixing a solubilized silk protein solution, a film-forming polymer, a plasticizer, and chilled water, and then transferring the mixture to a jacket-heated tank. These components can be mixed at ambient temperature (18-22° C.). The mixture can then be cooked (for example at a temperature ranging from 57-95° C.) under vacuum for a short period (e.g., 15-30 minutes) to form a homogenous, deaerated shell material. Additional shell additives can be added to the mixture at any point during the gel manufacturing process, or they may be incorporated into the finished homogenous shell material using a high torque mixer.

The hot melt process can involve adding, under mild agitation, a solubilized silk protein solution and a film-forming polymer to a preheated (e.g., 60-80° C.) mixture of plasticizer and water, and stirring the blend until complete melting is achieved. While the hot melt process is faster than the cold melt process, it is less accurately controlled and more susceptible to foaming and dusting.

Hard and soft capsules can be formed from the homogeneous shell mixture using methods known in the art. For example, soft capsules can be produced from the homogeneous shell mixture using a rotary die encapsulation process. In this method, the homogeneous shell mixture is fed either by gravity or through positive displacement pumping to two heated (e.g., 48-65° C.) metering devices. The metering devices control the flow of the homogeneous shell mixture into cooled (e.g., 10-18° C.), rotating casting drums. Ribbons are formed as the cast from the homogeneous shell mixture set on contact with the surface of the drums. The ribbons can then be fed through a series of guide rolls and between injection wedges and the capsule-forming dies. A food-grade lubricant oil can be applied onto the ribbons to reduce their tackiness and facilitate their transfer. Suitable lubricants include mineral oil, medium chain triglycerides, and soybean oil. Fill formulations can be fed into the encapsulation machine by gravity. The fill can be deaerated prior to encapsulation in a soft gelatin capsule. In some embodiments, the soft capsules contain printing on the surface, optionally identifying the encapsulated agent and/or dosage.

The examples below are intended to further illustrate certain aspects of the methods and compositions described herein, and are not intended to limit the scope of the claims. It will be readily apparent to one of ordinary skill in the relevant arts that suitable modifications and adaptations to the compositions, methods, and applications described herein can be made without departing from the scope of any embodiments or aspects thereof. Having now described the various embodiments of the inventions in detail, the same will be more clearly understood by reference to the following examples, which are included herewith for purposes of illustration only and are not intended to be limiting. The scope of the compositions and methods described herein include all actual or potential combinations of embodiments, aspects, examples, and preferences herein described.

EXAMPLES

Example 1

Preparation of Silk Polymer Stock Solutions

Raw silk fibers (obtained from *Bombyx mori*) were degummed with degumming solution (0.25% Sodium carbonate, 0.25% Sodium dodecyl sulfate in deionized water). Raw silk fibers were boiled for two cycles at 80-90° C. in degumming solution for 1 hour per cycle. Following boiling, the degummed silk fibers were rinsed thoroughly with hot tap water and deionized water. Degummed silk fibers were boiled in DI water at 80-90 C for 1 hour. Approximately 20-30% of sericin by weight was removed from the initial raw silk fiber. Following completion of degumming, the silk fibers were SF fibers that contained less than 1% by weight sericin.

The SF fibers were dissolved in a $CaCl_2$:EtOH:$H_2O$ (1:2:8 molar ratio) solvent system. Dissolved SF was dialyzed using cellulose membrane (Molecular Weight Cut-Off (MWCO): 3,000-5,000 Da) to form ~5% by weight solubilized SF solution, which was blended with gelatin masses, as described below.

A 15% by weight solution of silk fibroin powder (MW=100 kDa, Arch Personal Care Products, L.P., South Plainfield, N.J.) in $CaCl_2$:EtOH:$H_2O$ (1:2:8 molar ratio) was prepared. The dissolved silk fibroin powder was dialyzed using cellulose membrane (MWCO: 3,000-5,000 Da) to form ~5% solubilized silk fibroin powder solution, which was blended gelatin masses, as described below.

Preparation of Gelatin Masses

Gelatin masses were prepared as follows. A gel mass (44% by weight gelatin, 10% by weight glycerin, 34% by weight water, and 12% by weight sorbitol) was blended with varying amounts of silk solution to provide a gelatin mass, as detailed in Table 1.

TABLE 1

| Components of gelatin masses (50 g) | | | | |
|---|---|---|---|---|
| | Blends of Gel:Silk Soln (1.18 wt %) w/w | | | |
| | 90/10 blend | 80/20 blend | 70/30 blend | 60/40 blend |
| Silk solution (g) | 5 | 10 | 15 | 20 |
| Gel Mass (g) | 45 | 40 | 35 | 30 |
| Water from silk (g) | 4.94 | 9.88 | 14.82 | 19.76 |
| Weight percent silk in gel | 0.12 | 0.24 | 0.35 | 0.47 |

After mixing, the gelatin masses were aged for 12 or 24 hours, depending on the level of the plasticizers and the type of gelatin employed.

The viscosities of the gelatin masses were measured using a Brookfield Viscometer prior to selecting the appropriate composition for making capsules using a PEG-based fill.

The gelatin masses had suitable viscosities for the formation of capsule shells (e.g., ranging from 6,000 to 13,000 cP).

Analysis of the Structure of the Silk Polymers in Solution and In Combination with Gelatin Masses Silk fibroin can adopt a β-sheet or random coil structure, depending on its concentration and environment. The structure of silk fibroin can be evaluated by measuring characteristic IR absorption bands associated with the amide bonds in the silk fibroin backbone.

TABLE 2

Characteristic IR absorption bands associated with silk fibroin adopting a random coil structure and β-sheet structure.

| Protein Vibrational | Amide I | | Amide II | |
|---|---|---|---|---|
| Band | Random Coil | β-Sheet | Random Coil | β-Sheet |
| Wavenumber (cm$^{-1}$) | 1650 | 1630 | 1540 | 1520 |

Preparation of Soft Capsules Using Solubilized Silk Polymers

Preparation of Soft Capsules Using a Solubilized SF Solution

Based on the viscosity measurements described above, a 90:10 ratio of gelatin mass:solubilized SF solution was selected for use during the encapsulation process. A PEG-based fill was used as a model fill for encapsulation.

Soft capsules were prepared using a rotary die process in which a molten mass of a gelatin-based sheath formulation was fed from a reservoir onto cooled drums to form two spaced sheets or ribbons of the gelatin-based formulation in a semi-molten state. The ribbon thickness for the soft gelatin capsules was 0.035 inches (≈0.89 mm). These ribbons were fed around rollers and brought together at a convergent angle into the nip of a pair of roller dies that include opposed die cavities. The material to be encapsulated was fed into the wedge-shaped joiner of the ribbons. The gelatin ribbons were continuously conveyed between the dies, with portions of the fill being trapped between the sheets inside the die cavities. The sheets were then pressed together, and severed around each die so that opposed edges of the sheets flowed together to form a continuous gelatin-based sheath around the entrapped fill. The part of the gelatin-based sheath that is severed from the segments forming the capsules was collected and discarded or recycled. The soft capsules are then dried to increase the integrity of the sheath. The capsules were initially dried in a tumble drier for 30 minutes before being spread evenly on trays. Then there were further dried in a Bryant Drier at 25° C. and at 18% relative humidity.

Preparation of Soft Capsules Using a Solubilized Silk Fibroin Powder Solution

Based on the viscosity measurements described above, a 95:5 ratio of gel mass:solubilized silk fibroin powder solution was chosen for the encapsulation process. The solubilized silk fibroin powder solution concentration before addition to the gelatin mass was 5.67%. Soft capsules were prepared using the method described above for soft capsules formed using the solubilized SF solution.

Soft Capsule Stability Over Time

Capsules formed using the solubilized SF solution (15 count) were placed into 60 cc bottles and evaluated for stability under storage at three different conditions: Room Temperature, 30° C./60% RH and 40° C./75% RH. Soft gelatin capsules (not including silk) were also evaluated under the same conditions. The following stability scheme was used:

Room Temperature: 1, 3, 6, 12, 24 months
30° C./65% RH: 1, 3, 6 months
40° C./75% RH: 1, 2, and 3 months Samples were removed at the above-mentioned time points, and capsules were assessed for physical stability and dissolution performance. The results are detailed in Table 4.

TABLE 4

Comparison of the stability of soft gelatin capsules without silk and soft capsules formed using solubilized SF solution

| Sample | 1 month | 2 month | 3 month |
|---|---|---|---|
| Soft Gelatin Capsules (Without Silk) | | | |
| Room Temperature | No Leakers | — | No Leakers |
| 30° C./65% RH | Leakers | — | Leakers |
| 40° C./75% RH | Leakers | Leakers | Leakers |
| Capsules Formed Using the Solubilized SF Solution | | | |
| Room Temperature | No Leakers | — | No Leakers |
| 30° C./65% RH | No Leakers | — | No Leakers |
| 40° C./75% RH | No Leakers | No Leakers | No Leakers |

During the course of storage, the soft gelatin capsules formed a clump and more than 80% of the fill leaked out from the capsules, indicating that the seams were very weak. The capsules formed using the solubilized silk polymer held out much better at the stressed conditions, with minimal clumping and no leakage from the seams.

By 3 months (storage at 40° C./75% RH), the soft gelatin capsules clump together. Most of the fill leaked out from the shell because of weakened capsule seams. In contrast, the silk-based capsules hold up well and pass the physical attributes specifications at 1 month and 3 month 40° C./75% RH.

Dissolution Performance of Capsules Formed Using Solubilized Silk Polymers

The dissolution performance of soft capsules containing a fill and a shell formed using the solubilized SF solution was compared with soft gelatin capsules without silk at Time Zero at pH 7.4. The dissolution parameters were:

Apparatus: Paddles
Agitation Rate: 50 rpm
Dissolution volume: 500 mL

Figure 1:
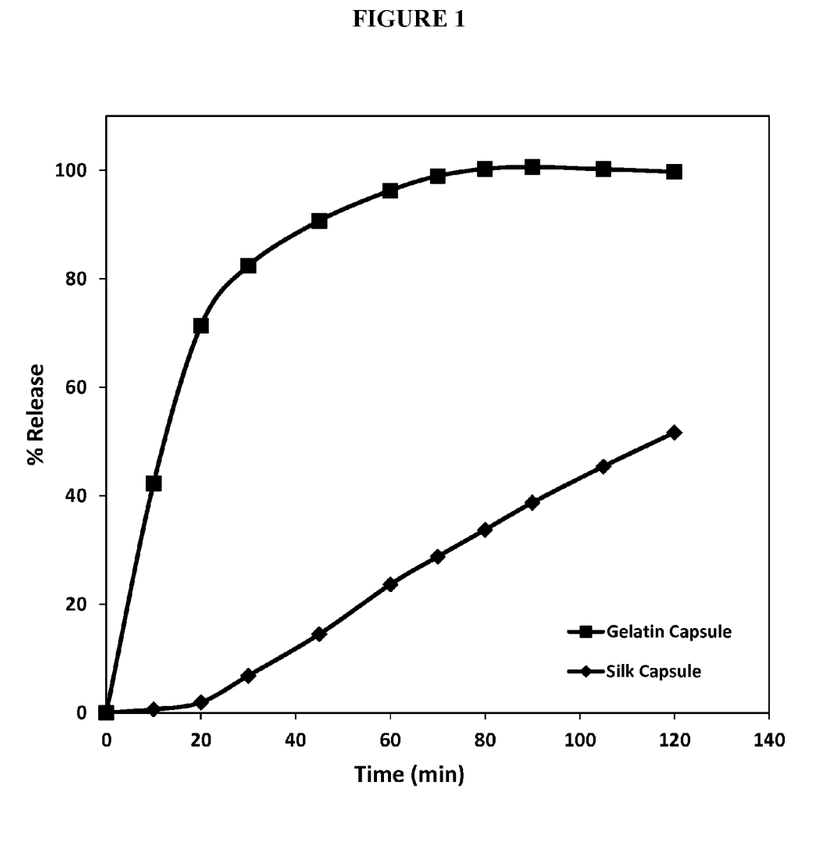
FIG. 1 shows a plot of the percent of fill released from gelatin soft capsules (square trace) and silk-based soft capsules (diamond trace) as a function of time (in minutes).

The soft gelatin capsules without silk were completely dissolved after 60 minutes; all of the fill was dispersed and dissolved in the dissolution media (See FIG. 1, square trace). The solubilized SF solution capsules showed minimal signs of seam breakage. In addition, the dissolution rate of the gelatin was dramatically decreased. The shell of the solubilized SF solution capsules remained floating in the dissolution vessel even after all the fill was dispersed.

This demonstrates that the incorporation of 0.3% solubilized SF solution in the gelatin mass provides a robust shell that exhibits controlled release of the fill contents.

Figure 2:
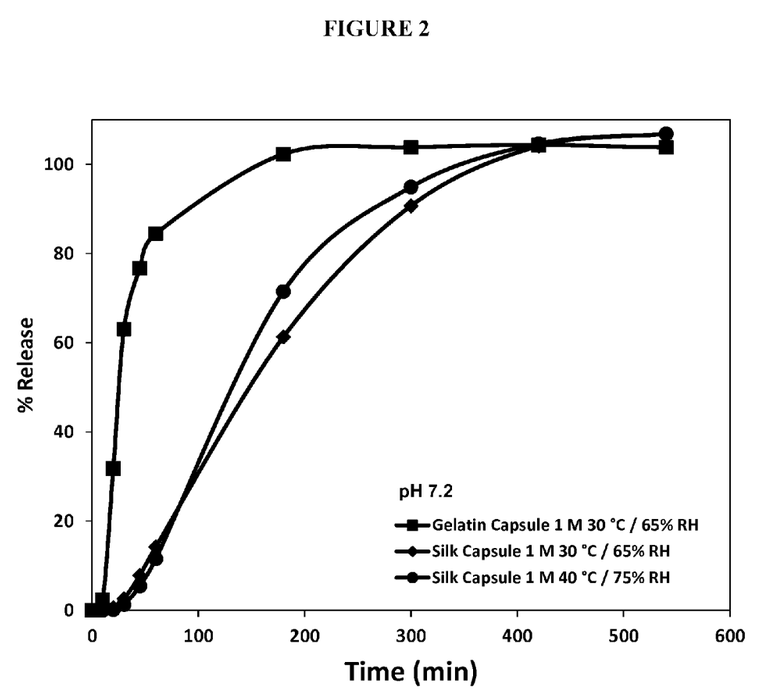
FIG. 2 shows a plot of the percent of fill released from gelatin soft capsules stored for 1 month at 30° C./65% RH (square trace), silk-based soft capsules stored for 1 month at 30° C./65% RH (diamond trace), and silk-based soft capsules stored for 1 month at 40° C./75% RH (circle trace) as a function of time (in minutes).

The solubilized SF solution capsules stored for 1 month at 30° C./65% RH and 40° C./75% RH were also analyzed for dissolution performance compared to soft gelatin capsules without silk. The release of the fill contents was significantly lower from the silk-based capsules, suggesting that the interpenetrating network formed by the silk polymer and the gelatin helps maintain the controlled release properties of the capsules (See FIG. 2). To level of controlled release could be modulated by loading the gelatin mass with lesser amounts of silk protein (<0.3%).

Figure 3:
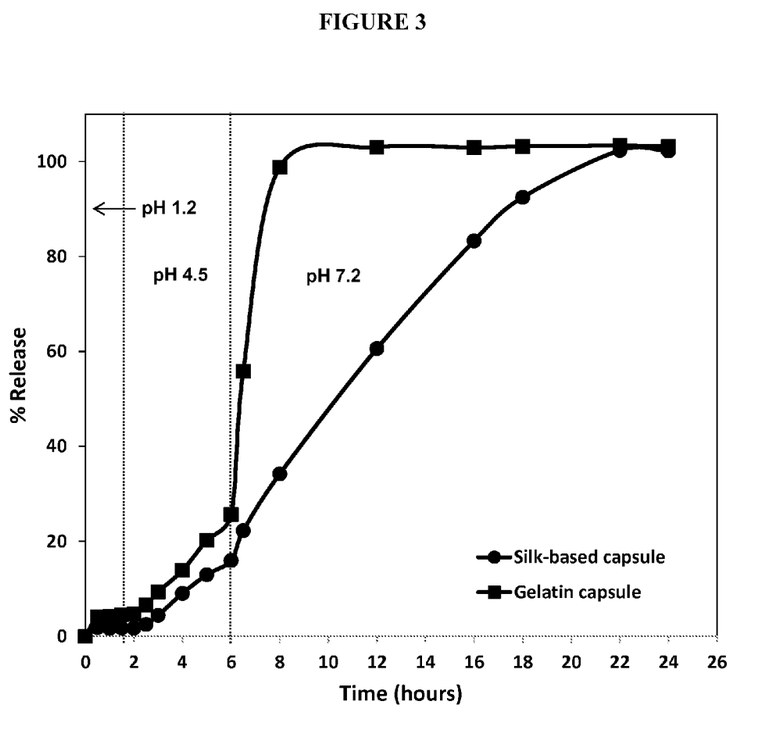
FIG. 3 is the plot of the percent of fill released from gelatin soft capsules (square trace) and silk-based soft capsules (circle trace) as a function of time during the course of a 3-stage dissolution experiment. The pH was varied from 1.2 (first two hours) to 4.5 (next four hours) to 7.2 (final 18 hours).

Three-stage dissolution was also employed to assess the performance of silk-based capsules compared to soft gelatin capsules without silk and spray dried silk microparticles. As shown in FIG. 3, the silk-based capsules performed identical to the soft gelatin capsules without silk and the microparticles in pH 1.2 and pH 4.5 conditions. At pH 7.2, we see a burst release from the soft gelatin capsules without silk, whereas the dissolution from the silk capsules and the spray-dried particles follows a controlled pattern releasing 100% of the drug by the end of 18 hours. The incorporation of 0.3% silk in the gelatin capsules provides a release profile that is commensurate to the release achieved with the microparticles that are loaded with a high silk content.

The capsules and methods of the appended claims are not limited in scope by the specific capsules and methods described herein, which are intended as illustrations of a few aspects of the claims and any capsules and methods that are functionally equivalent are intended to fall within the scope of the claims. Various modifications of the capsules and methods in addition to those shown and described herein are intended to fall within the scope of the appended claims. Further, while only certain representative capsules and method steps disclosed herein are specifically described, other combinations of the capsules and method steps are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated.

What is claimed is:

1. A soft capsule comprising a capsule shell and a fill material, wherein the capsule shell consists essentially of 0.28% of silk fibroin by weight of the capsule shell; 41.8% of gelatin by weight of the capsule shell; 9.5% of glycerol by weight of the capsule shell; 11.4% of sorbitol by weight of the capsule shell; and 37.0% of water by weight of the capsule shell; and wherein the soft capsule provides extended release of the fill material at pH 7.2.

2. The soft capsule of claim 1, wherein the silk fibroin comprises an average molecular weight ranging from 50 kDa to 450 kDa.

3. The soft capsule of claim 1, wherein the fill material comprises one or more pharmaceutical agents.

4. The soft capsule of claim 1, wherein the fill material comprises one or more pharmaceutically acceptable excipients.

5. The soft capsule of claim 1, wherein the silk fibroin comprise *Bombyx mori* silk fibroin.

6. The soft capsule of claim 1, wherein the silk fibroin has a molecular weight of 100 kDa.

* * * * *